United States Patent
Abd Elaal (10) Patent No.: US 11,717,325 B2
(45) Date of Patent: Aug. 8, 2023

(54) MEDICATED UTERINE BALLOON WITH CERVICAL BARRICADE FOR MANAGEMENT OF POSTPARTUM HEMORRHAGE

(71) Applicant: Nasser Kamal Abd Elaal, Dakahleia (EG)

(72) Inventor: Nasser Kamal Abd Elaal, Dakahleia (EG)

(*) Notice: Subject to any disclaimer, the term of this patent is extended or adjusted under 35 U.S.C. 154(b) by 590 days.

(21) Appl. No.: 16/632,590

(22) PCT Filed: Dec. 3, 2017

(86) PCT No.: PCT/EG2017/000031
§ 371 (c)(1),
(2) Date: Jan. 21, 2020

(87) PCT Pub. No.: WO2019/105519
PCT Pub. Date: Jun. 6, 2019

(65) Prior Publication Data
US 2020/0187985 A1    Jun. 18, 2020

(51) Int. Cl.
*A61B 17/42*  (2006.01)
*A61M 25/10*  (2013.01)
(Continued)

(52) U.S. Cl.
CPC .......... *A61B 17/42* (2013.01); *A61K 31/195* (2013.01); *A61M 25/1002* (2013.01);
(Continued)

(58) Field of Classification Search
None
See application file for complete search history.

(56) References Cited

U.S. PATENT DOCUMENTS 5,935,098 A * 8/1999 Blaisdell ............... A61M 25/04
                                                          604/515
6,555,124 B1   4/2003 Kolter
(Continued)

FOREIGN PATENT DOCUMENTS

CN   200984216 Y  * 12/2007  ....... A61B 17/12099
CN   200984216 Y    12/2007
(Continued)

OTHER PUBLICATIONS

English language translation of CN 200984216 Y. (Year: 2007).*
(Continued)

*Primary Examiner* — Dominic Lazaro
(74) *Attorney, Agent, or Firm* — Laurie A. Schlichter, PLLC (57) ABSTRACT

A device for managing postpartum hemorrhage is described. The device comprises an intrauterine balloon that may be deflated when inserted into a uterine cavity. The intrauterine balloon may be inflated inside the uterine cavity. The device also comprises a drug delivery vehicle that may be deposited on an outer surface of the intrauterine balloon by a coating technique or an eluting technique. The drug delivery vehicle may release a hemostatic drug into the uterine cavity. The device additionally comprises a cervical barricade that may retain the released hemostatic drug in the uterine cavity. The cervical barricade may be a cone-shaped plug that tapers proximally to conform to a contour of a vagina. The device further comprises a catheter that may be used to inflate the intrauterine balloon, deflate the intrauterine balloon, and support the cervical barricade.

16 Claims, 2 Drawing Sheets

(51) Int. Cl.
*A61K 31/195* (2006.01)
*A61B 17/12* (2006.01)
*A61K 9/14* (2006.01)
*B82Y 5/00* (2011.01)

(52) U.S. Cl.
CPC ....... *A61B 2017/12004* (2013.01); *A61K 9/14* (2013.01); *A61M 2025/105* (2013.01); *A61M 2210/1433* (2013.01); *B82Y 5/00* (2013.01)

(56) References Cited

U.S. PATENT DOCUMENTS

| | | | | |
|---|---|---|---|---|
| 6,827,703 | B1* | 12/2004 | Ackerman | A61M 25/10 |
| | | | | 604/99.04 |
| 7,879,966 | B2* | 2/2011 | Petereit | A61P 25/16 |
| | | | | 524/823 |
| 8,123,773 | B1 | 2/2012 | Shirley | |
| 2003/0143315 | A1* | 7/2003 | Pui | B05B 5/025 |
| | | | | 427/2.24 |
| 2007/0231363 | A1* | 10/2007 | Chen | A61L 31/16 |
| | | | | 514/327 |
| 2008/0181928 | A1* | 7/2008 | Hakimi-Mehr | A61P 35/00 |
| | | | | 427/2.25 |
| 2015/0202411 | A1* | 7/2015 | Duncan | A61M 25/04 |
| | | | | 604/544 |
| 2016/0317434 | A1* | 11/2016 | Kastrup | A61K 38/4833 |

FOREIGN PATENT DOCUMENTS

| | | |
|---|---|---|
| CN | 203089264 U | 7/2013 |
| CN | 203424985 U | 2/2014 |
| CN | 105708514 A | 6/2016 |
| CN | 205612515 U | 10/2016 |
| WO | 2015089626 A1 | 6/2015 |
| WO | 2015112475 A1 | 7/2015 |

OTHER PUBLICATIONS

ACOG Practice Bulletin No. 76: Postpartum Hemorrhage. Obstetrics & Gynecology, vol. 108, No. 4, Oct. 2006, pp. 1039-1047 [online], [retrieved on Oct. 23, 2019]. Retrieved from the Internet <URL: https://pqcnc-documents.s3.amazonaws.com/aim/aimexpert/PQCNCOBHACOGPracticeBulletinPPHemorrhage200610%20.pdf> <DOI: 10.1097/00006250-200610000-00046>.

Khan, KS et al. WHO analysis of causes of maternal death: a systematic review. The Lancet, vol. 367, No. 9516, Apr. 1, 2006, pp. 1066-1074 [online], [retrieved on Oct. 14, 2019]. Retrieved from the Internet <URL: https://u.demog.berkeley.edu/~jrw/Biblio/Eprints/%20J-L/khan.etal.2006_maternal.causes.review_Lancet.pdf> <DOI: 10.1016/S0140-6736(06)68397-9>.

Lalonde, A et al. Postpartum hemorrhage today: ICM/FIGO initiative 2004-2006. International Journal of Gynecology & Obstetrics, vol. 94, No. 3, Jul. 12, 2006, pp. 243-253 [online], [retrieved on Oct. 14, 2019]. Retrieved from the Internet <URL: https://obgyn.onlinelibrary.wiley.com/doi/epdf/10.1016/j.ijgo.2006.04.016> <DOI: 10.1016/j.ijgo.2006.04.016>.

Bakri, YN et al. Tamponade-balloon for obstetrical bleeding. International Journal of Gynecology & Obstetrics, vol. 74, No. 2, Aug. 7, 2001, pp. 139-142 [online], [retrieved on Oct. 23, 2019]. Retrieved from the Internet <URL: https://www.academia.edu/1397662/Tamponade-balloon_for_obstetrical_bleeding> <DOI: 10.1016/S0020-7292(01)00395-2>.

Dildy, G. A. and Clark, S. L. Postpartum hemorrhage, in: Contemporary OB/GYN, vol. 38 (Aug. 1993), pp. 21-29.

Condous, GS et al. The "Tamponade Test" in the Management of Massive Postpartum Hemorrhage. Obstetrics & Gynecology, vol. 101, No. 4, Apr. 2003, pp. 767-772 [online], [retrieved on Oct. 14, 2019]. Retrieved from the Internet <URL: https://journals.lww.com/greenjournal/Fulltext/2003/04000/The_Tamponade_Test_in_the_Management_of_Massive.26.aspx> <DOI: 10.1016/S0029-7844(03)00046-2>.

Chantrapitak, W et al. The Efficacy of Lower Uterine Segment Compression for Prevention of Early Postpartum Hemorrhage after Vaginal Delivery. The Journal of the Medical Association of Thailand, vol. 94, No. 6, Jun. 2011, pp. 649-656 [online], [retrieved on Oct. 14, 2019]. Retrieved from the Internet <URL: http://www.thaiscience.info/journals/Article/JMAT/10817117.pdf>.

Peitsidis, P et al. Antifibrinolytic therapy with tranexamic acid in pregnancy and postpartum. Expert Opinion on Pharmacotherapy, vol. 12, No. 4, Feb. 4, 2011, pp. 503-516 [online], [retrieved on Oct. 23, 2019]. Retrieved from the Internet <URL: https://www.tandfonline.com/doi/full/10.1517/14656566.2011.545818?scroll=top&needAccess=true> <DOI: 10.1517/14656566.2011.545818>.

Ker, K et al. Effect of tranexamic acid on surgical bleeding: systematic review and cumulative meta-analysis. The British Medical Journal, vol. 344, No. 7858, May 21, 2012, e3054 [online], [retrieved on Oct. 14, 2019], Retrieved from the Internet <URL: https://www.bmj.com/content/bmj/344/bmj.e3054.full.pdf> <DOI: 10.1136/bmj.e3054>.

Crash-2 Trial Collaborators. Effects of tranexamic acid on death, vascular occlusive events, and blood transfusion in trauma patients with significant haemorrhage (CRASH-2): a randomised, placebo-controlled trial. The Lancet, vol. 376, No. 9734, Jul. 3, 2010, pp. 23-32 [online], [retrieved on Oct. 14, 2019]. Retrieved from the Internet <URL: https://www.thelancet.com/pdfs/journals/lancet/PIIS0140-6736(10)60835-5.pdf><DOI: 10.1016/S0140-6736(10)60835-5>.

Dell'Amore, A et al. Can Topical Application of Tranexamic Acid Reduce Blood Loss in Thoracic Surgery? A Prospective Randomised Double Blind Investigation. Heart, Lung and Circulation, vol. 21, No. 11, Nov. 2012, pp. 706-710 [online], [retrieved on Oct. 22, 2019]. Retrieved from the Internet <URL: https://www.heartlungcirc.org/article/S1443-9506(12)01111-0/fulltext> <DOI: 10.1016/j.hlc.2012.06.016>.

Fawzy, H et al. Can local application of Tranexamic acid reduce post-coronary bypass surgery blood loss? A randomized controlled trial. Journal of Cardiothoracic Surgery, vol. 4, No. 25, Jun. 18, 2009 [online], [retrieved on Oct. 14, 2019]. Retrieved from the Internet <URL: https://cardiothoracicsurgery.biomedcentral.com/track/pdf/10.1186/1749-8090-4-25> <DOI: 10.1186/1749-8090-4-25>.

Wong, J et al. Topical Application of Tranexamic Acid Reduces Postoperative Blood Loss in Total Knee Arthroplasty. The Journal of Bone & Joint Surgery, vol. 92-A, No. 15, Nov. 3, 2010, pp. 2503-2513 [online], [retrieved on Oct. 14, 2019]. Retrieved from the Internet <URL: http://www.stopbang.ca/publication/pdf/pub41.pdf> <DOI: 10.2106/JBJS.I.01518>.

Kinugasa, M et al. Uterine Balloon Tamponade in Combination with Topical Administration of Tranexamic Acid for Management of Postpartum Hemorrhage. Case Reports in Obstetrics and Gynecology, vol. 2015, Mar. 12, 2015 [online], [retrieved on Oct. 18, 2019] Retrieved from the Internet <URL: http://downloads.hindawi.com/journals/criog/2015/195036.pdf> <DOI: 10.1155/2015/195036>.

Rafeey, M et al. Topical tranexamic acid as a novel treatment for bleeding peptic ulcer: A randomised controlled trial. African Journal of Paediatric Surgery, vol. 13, No. 1, Jan.-Mar. 2016, pp. 9-13 [online], [retrieved on Oct. 18, 2019]. Retrieved from the Internet <URL: https://search.proquest.com/openview/eb9c284a3757582e18d883b6e44f0c00/1?pq-origsite=gscholar&cbl=226536> <DOI: 10.4103/0189-6725.181700>.

Woman Trial Collaborators. Effect of early tranexamic acid administration on mortality, hysterectomy, and other morbidities in women with post-partum haemorrhage (WOMAN): an international, randomised, double-blind, placebo-controlled trial. The Lancet, vol. 389, No. 10084, May 27, 2017, pp. 2105-2116 [online], [retrieved on Oct. 18, 2019]. Retrieved from the Internet <URL: https://www.thelancet.com/pdfs/journals/lancet/PIIS0140-6736(17)30638-4 pdf> <DOI: 10.1016/S0140-6736(17)30638-4>.

Seidlitz, A et al. In Vitro Determination of Drug Transfer from Drug-Coated Balloons. PLoS ONE, vol. 8, No. 12, Dec. 31, 2013 [online], [retrieved on Oct. 18, 2019]. Retrieved from the Internet (56) References Cited

OTHER PUBLICATIONS

<URL: https://journals.plos.org/plosone/article/file?id=10.1371/journal.pone.0083992&type=printable> <DOI: 10.1371/journal.pone.0083992>.

James, HP et al. Smart polymers for the controlled delivery of drugs—a concise overview. Acta Pharmaceutica Sinica B, vol. 4, No. 2, Apr. 2014, pp. 120-127 [online], [retrieved on Oct. 18, 2019], Retrieved from the Internet <URL http://citeseerx.ist.psu.edu/viewdoc/download?doi=10.1.1.791.3272&rep=rep1&type=pdf> <DOI: 10.1016/j.apsb.2014.02.005>.

Baylis, JR et al. Halting hemorrhage with self-propelling particles and local drug delivery. Thrombosis Research, vol. 141S2, May 1, 2016, pp. S36-S39 [online], [retrieved on Oct. 23, 2019], Retrieved from the Internet <URL: https://shop.tarjomeplus.com/UploadFileEn/TPLUS_EN_4371.pdf> <DOI: 10.1016/S0049-3848(16)30362-0>.

Egyptian Patent Office, International Search Report for PCT/EG2017/000031, dated Jan. 28, 2018 [online], [retrieved on Oct. 18, 2019].

University of British Columbia. Treating Postpartum Hemorrhage with a Low-Cost Intrauterine Formulation of Tranexamic Acid. Saving Lives at Birth, 2016 [online], [retrieved on Oct. 9, 2019]. Retrieved from the Internet <URL: https://savinglivesatbirth.net/summaries/2016/508>.

Treating Postpartum Hemorrhage with a Low-Cost Intrauterine Formulation of Tranexamic Acid. YouTube [online] [video]. Saving Lives at Birth: A Grand Challenge for Development (SavingLivesGCD), Sep. 7, 2016 [retrieved on Oct. 9, 2019], Retrieved from the Internet <URL: https://www.youtube.com/watch?v=lcXc4hO4SSU>.

University of British Columbia. UBC researchers create self-propelled powder to stop bleeding. Oct. 2, 2015 [online], [retrieved on Oct. 9, 2019]. Retrieved from the Internet <URL: https://news.ubc.ca/2015/10/02/ubc-researchers-create-self-propelled-powder-to-stop-bleeding>.

Self-propelled powder stops severe bleeding. YouTube [online] [video]. University of British Columbia (UBC Media Relations), Oct. 2, 2015 [retrieved on Oct. 9, 2019], Retrieved from the Internet <URL: https://www.youtube.com/watch?v=08X9QB-2miA&feature=youtu.be>.

Egyptian Patent Office, Written Opinion of the International Searching Authority for PCT/EG2017/000031, dated Jan. 28, 2018 [online], [retrieved on Oct. 23, 2019].

Park, S et al. Layer-by-layer assembled polymeric thin films as prospective drug delivery carriers: design and applications. Biomaterials Research, vol. 22, No. 29, Sep. 26, 2018 [online], [retrieved on Nov. 1, 2019]. Retrieved from the Internet <URL: https://biomaterialsres.biomedcentral.com/track/pdf/10.1186/s40824-018-0139-5> <DOI: 10.1186/s40824-018-0139-5>.

Ramakrishna, CD et al. Basic Concepts and Clinical Outcomes of Drug-Eluting Balloons for Treatment of Coronary Artery Disease: An Overview. Journal of Clinical and Diagnostic Research, vol. 11, No. 6, Jun. 1, 2017, pp. OE01-OE04 [online], [retrieved on Nov. 1, 2019]. Retrieved from the Internet <URL: https://www.ncbi.nlm.nih.gov/pmc/articles/PMC5535426/pdf/jcdr-11-OE01.pdf> <DOI: 10.7860/JCDR/2017/26321.10000>.

Turner, EA et al. Coating and pharmacokinetic evaluation of air spray coated drug coated balloons. Cardiovascular Engineering and Technology, vol. 9, No. 2, Jun. 2018, pp. 240-250 [online], [retrieved on Jan. 25, 2020], Retrieved from the Internet <URL: https://www.ncbi.nlm.nih.gov/pmc/articles/PMC5990435/pdf/nihms947501.pdf> <DOI: 10.1007/s13239-018-0346-1>.

Zylberberg, C et al. Pharmaceutical liposomal drug delivery: a review of new delivery systems and a look at the regulatory landscape. Drug Delivery, vol. 23, No. 9, May 5, 2016, pp. 3319-3329 [online], [retrieved on Nov. 1, 2019]. Retrieved from the Internet <URL: https://www.tandfonline.com/doi/pdf/10.1080/10717544.2016.1177136?needAccess.=true> <DOI: 10.1080/10717544.2016.1177136>.

Baylis, JR et al. Self-propelled particles that transport cargo through flowing blood and halt hemorrhage. Science Advances, vol. 1, No. 9, Oct. 2, 2015 [online], [retrieved on Feb. 1, 2020]. Retrieved from the Internet <URL: https://advances.sciencemag.org/content/advances/1/9/e1500379.full.pdf> <DOI: 10.1126/sciadv.1500379>.

Livingston, M et al. Coating Techniques and Release Kinetics of Drug-Eluting Stents. Journal of Medical Devices, vol. 10, No. 1, Mar. 2016, pp. 010801-1-010801-8 [online], [retrieved on Feb. 1, 2020]. Retrieved from the Internet <URL: https://www.researchgate.net/profile/Megan_Livingston/publication/282593383_Coating_Techniques_and_ Release_Kinetics_of_Drug-Eluting_Stents/links/5b19c8ba45851587f29befad/Coating-Techniques-and-Release-Kinetics-of-Drug-Eluting-Stents.pdf> <DOI: 10.1115/1.4031718>.

Lee, D et al. The Newest Generation of Drug-eluting Stents and Beyond. European Cardiology Review, vol. 13, No. 1, Aug. 2018, pp. 54-59 [online], [retrieved on Feb. 1, 2020]. Retrieved from the Internet <URL: https://www.ncbi.nlm.nih.gov/pmc/articles/PMC6159420/pdf/ecr-13-1-54.pdf> <DOI: 10.15420/ecr.2018:8:2>.

* cited by examiner

MEDICATED UTERINE BALLOON WITH CERVICAL BARRICADE FOR MANAGEMENT OF POSTPARTUM HEMORRHAGE

TECHNICAL FIELD

The present disclosure relates generally to devices for managing postpartum hemorrhage. More specifically, the present disclosure relates to a device having mechanical and pharmacological mechanisms for managing postpartum hemorrhage.

BACKGROUND ART

Various techniques are used to manage postpartum hemorrhage. Uterotonic medications are usually the first choice for treatment of excessive and continuous postnatal bleeding. Uterotonics cause contraction of the uterus which should stop the hemorrhage. If heavy blood loss persists, uterine massage may be initiated to induce the uterus to contract. Uterine balloon tamponade (UBT) is recommended if uterotonics and uterine massage fail to staunch the hemorrhage. In UBT, a balloon is inserted into the uterus and inflated. The balloon presses against the uterine lining to stop the bleeding.

The same numbers are used throughout the disclosure and the figures to reference like components and features. Numbers in the 100 series refer to features originally found in FIG. 1. Numbers in the 200 series refer to features found in FIG. 2.

DESCRIPTION OF THE EMBODIMENTS

Postpartum hemorrhage (PPH) is the leading cause of maternal mortality worldwide. It is responsible for one-fourth of all delivery-related deaths. Consequently, several strategies for managing PPH have been developed. Treatment options include the administration of uterotonic medications and the application of pressure to the uterus by uterine massage or balloon tamponade. These treatment options result in either a mechanical effect or a pharmacological effect. A single intervention having both effects may be a more efficient and efficacious solution for reducing the morbidity and mortality caused by PPH.

Pharmaceutical treatment of PPH involves the use of uterotonics administered intravenously or intramuscularly. Other types of medication administered by other routes may be at least as effective as the current pharmaceutical regimen. For example, antifibrinolytic drugs promote clot formation and it has been demonstrated that they reduce maternal mortality from PPH when administered systemically. Topical administration would deliver antifibrinolytics to the uterine lining, the site of bleeding in PPH. An additional advantage of topical administration is the avoidance of serious thromboembolic disease which can occur with systemic administration of antifibrinolytics.

The lower uterine segment (LUS) may be the site of the hemorrhage. In particular, an abnormally implanted placenta or an abnormally adherent placenta may cause bleeding from the LUS. Hemorrhaging from the LUS may be severe because the LUS thins during the third trimester in preparation for the onset of labor. The pressure applied by an inflated intrauterine balloon may be insufficient to stop the bleeding. Accordingly, additional counter pressure may be needed to arrest the hemorrhage.

The subject matter disclosed herein relates to a device for managing PPH. The device may have both mechanical and pharmacological mechanisms for stopping a hemorrhage. The device may include a balloon located at one end of a catheter. The balloon may be placed in the uterine cavity and inflated. The inflated intrauterine balloon may apply pressure to the uterine lining and thereby contribute to the cessation of bleeding.

The inflated intrauterine balloon may serve as a drug delivery vehicle. An antifibrinolytic drug or any other hemostatic drug may be deposited on the outer surface of the balloon by a coating technique or an eluting technique. The drug may be released from the balloon and migrate to the lining of the uterine cavity where it exerts its hemostatic effect.

The device includes a cervical barricade that has several functions. The cervical barricade retains the released antifibrinolytic drug in the uterine cavity. As a result, the intrauterine residence time of the drug is long enough for the drug to achieve hemostasis. The cervical barricade resolves the problem of retaining a drug in an organ like the uterus which is hollow and open.

Furthermore, the cervical barricade may immobilize the inflated intrauterine balloon in the uterine cavity. Consequently, the outer surface of the inflated intrauterine balloon may continue to contact the uterine lining. Because of this apposition, the balloon may be more effective at applying pressure to the uterine lining and the released antifibrinolytic drug may have less distance to travel to reach the uterine lining and may achieve hemostasis more quickly. The immobilization of the balloon by the cervical barricade is necessary to attain these desired results. These results cannot be realized using a balloon that can change positions in the uterus. Hence, the immobilized balloon is preferable to a balloon that is free to move within the uterine cavity.

Lastly, the cervical barricade may apply the additional counter pressure necessary to arrest severe hemorrhage from the lower uterine segment. The pressure applied to the LUS by the inflated intrauterine balloon may be insufficient to control heavy bleeding. However, the pressure placed on the LUS by the inflated intrauterine balloon combined with the pressure placed on the LUS by the cervical barricade may be enough to stop a severe hemorrhage.

The present disclosure describes a device that manages PPH by both mechanical and pharmacological means. For example, the device may include an intrauterine balloon that may be deflated when inserted into a uterine cavity. The intrauterine balloon may be inflated once inside the uterine cavity. The device may also include a drug delivery vehicle deposited on an outer surface of the intrauterine balloon by a coating technique or an eluting technique. The drug delivery vehicle may release a hemostatic drug into the uterine cavity. The device may additionally include a cervical barricade that retains the released hemostatic drug in the uterine cavity. The cervical barricade may be a cone-shaped plug that tapers proximally to conform to a contour of a vagina. The device may further include a catheter used to inflate the intrauterine balloon, deflate the intrauterine balloon, and support the cervical barricade. Various examples of the present device are described below with reference to the figures.

Figure 1:
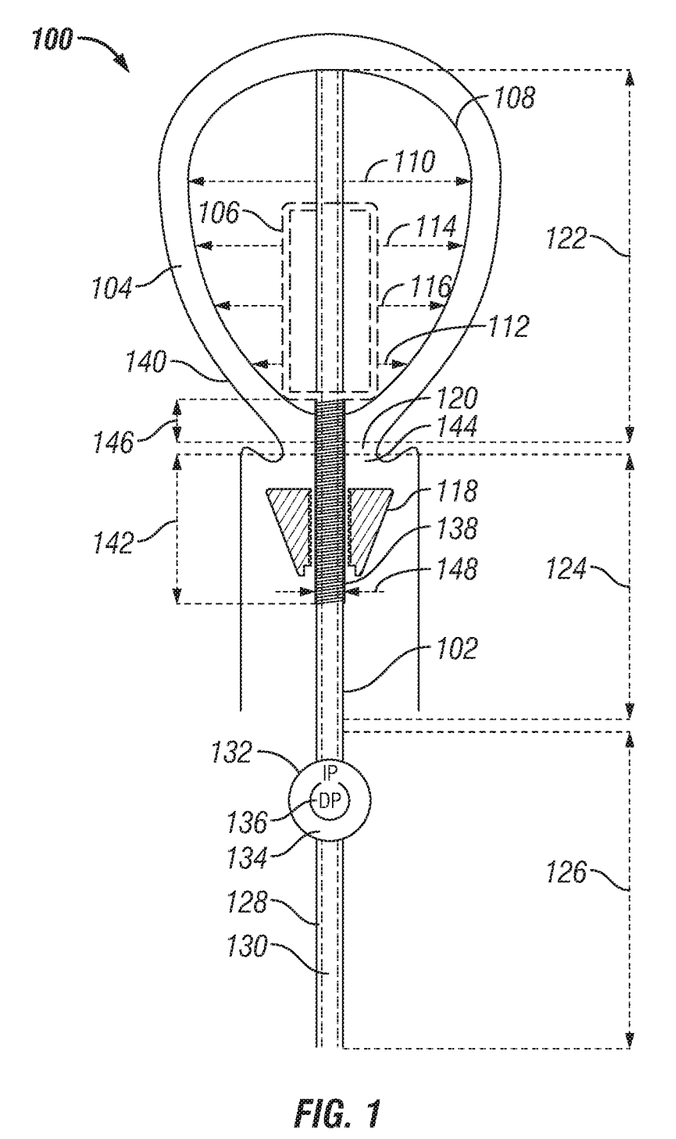
FIG. 1 is an illustration of a device for the management of postpartum hemorrhage.

FIG. 1 is an illustration of a device for the management of postpartum hemorrhage. The device 100 may include an intrauterine balloon located at an end of a catheter 102. The intrauterine balloon may be deflated when inserted into the uterine cavity 104.

The deflated intrauterine balloon 106 may be inflated once inside the uterine cavity 104. The inflated intrauterine balloon 108 may taper proximally. The distal diameter 110 may be approximately 80 mm while the proximal diameter 112 may be approximately 45 mm. Intermediate diameters 114, 116 may measure approximately 65 mm and 50 mm. These dimensions may change as the intrauterine balloon is inflated to a lesser or greater extent to accommodate variations in the size of the uterine cavity 104.

The inflated intrauterine balloon 108 may taper to conform to the lining of the uterine cavity 104. As a result, the outer surface of the inflated intrauterine balloon 108 may contact the lining of the uterine cavity 104. Because of this apposition, the outer surface of the inflated intrauterine balloon 108 may apply pressure to the lining of the uterine cavity 104. The application of pressure to the lining of the uterine cavity 104 may control PPH. To reduce uterine hemorrhage, the pressure applied to the lining of the uterine cavity 104 by the outer surface of the inflated intrauterine balloon 108 should be greater than systemic arterial pressure.

The application of pressure to the lining of the uterine cavity 104 is just one way the device 100 may manage PPH. The device 100 may control PPH by other means as well. The other means are discussed below.

The device 100 may include a drug delivery vehicle. A drug delivery vehicle may be a thin layer on the outer surface of the inflated intrauterine balloon 108. The thin layer may contain a hemostatic drug. The hemostatic drug may be transferred from the thin layer to the lining of the uterine cavity 104 when the outer surface of the inflated intrauterine balloon 108 contacts the lining of the uterine cavity 104. The delivery of the hemostatic drug to the lining of the uterine cavity 104 may reduce PPH.

There are several hemostatic drugs that may be included in the drug delivery vehicle on the outer surface of the inflated intrauterine balloon 108. The hemostatic drugs may include tranexamic acid, thrombin, fibrinogen, recombinant activated factor VII, and the like. These drugs may be used individually or in combination to arrest PPH.

Several techniques may be used to deposit the drug delivery vehicle on the outer surface of an intrauterine balloon. These techniques may include eluting techniques and coating techniques. The composition of the thin layer constituting the drug delivery vehicle differs depending upon the type of technique used. An eluting technique results in the application of a thin layer containing a polymer matrix. In contrast, the thin layer lacks a polymer matrix when a coating technique is used. As discussed below, the presence or absence of a polymer matrix may determine how the hemostatic drug is transferred from the thin layer on the outer surface of the inflated intrauterine balloon 108 to the lining of the uterine cavity 104.

Despite the difference in the composition of the thin layer, eluting techniques and coating techniques may share a method of manufacture. Whether made by eluting techniques or coating techniques, the thin layer is deposited on the outer surface of the intrauterine balloon while the balloon is inflated. Once the thin layer has dried, hemostatic drugs adhere to the inflated balloon in quantities sufficient to prevent significant drug loss during the subsequent deflation and folding of the balloon. Consequently, the deflated intrauterine balloon 106 can be inserted into the uterine cavity 104 and inflated to deliver therapeutic levels of the hemostatic drugs to the hemorrhage site in the uterine lining.

There may be two types of drug delivery vehicles. A drug delivery vehicle may be characterized by its method of manufacture. The first type may include drug delivery vehicles resulting from eluting techniques. The most effective of these drug delivery vehicles are biocompatible and biodegradable. Furthermore, the most effective drug delivery vehicles resulting from eluting techniques are designed to deliver the appropriate amount of a hemostatic drug to the lining of the uterine cavity 104. Many factors are considered when designing a drug delivery vehicle that will be manufactured by an eluting technique. Some of these factors include thin layer morphology, thin layer thickness, total drug load, drug transfer to the uterine cavity 104, drug loss, and residual drug concentration on the outer surface of the inflated intrauterine balloon 108.

As discussed above, drug delivery vehicles made by eluting techniques may be characterized by the presence of a polymer matrix in the thin layer on the outer surface of the inflated intrauterine balloon 108. A number of specialized polymers may constitute the polymer matrix. These specialized polymers may be hydrophilic or lipophilic. As a result, a number of different hemostatic drugs may associate with the polymer matrix. The polymers in the polymer matrix may include hydroxypropyl cellulose phthalate, hydroxypropyl methylcellulose phthalate, cellulose acetate phthalate, polyvinyl acetate phthalate, polyvinylpyrrolidone acetate, and the like. A polymer is selected to constitute the polymer matrix if the polymer results in the most efficient steady-state release of a hemostatic drug into the uterine cavity 104. The polymers may be used individually or in combination.

An embodiment of a drug delivery vehicle manufactured by an eluting technique may include nanoparticles of a hemostatic drug associated with the polymer matrix contained in the thin layer on the outer surface of the inflated intrauterine balloon 108. The thin layer may also include a first constituent and a second constituent. An interaction of the constituents may result in release of the nanoparticles of the hemostatic drug from the polymer matrix. The released nanoparticles of the hemostatic drug may contact the lining of the uterine cavity 104 where the released nanoparticles exert their antifibrinolytic effect.

The second type of drug delivery vehicle may include drug delivery vehicles resulting from coating techniques. Like drug delivery vehicles made by eluting techniques, drug delivery vehicles made by coating techniques may include a thin layer on the outer surface of an inflated intrauterine balloon 108. However, as discussed above, drug delivery vehicles manufactured by coating techniques may lack a polymer matrix.

The design of drug delivery vehicles resulting from coating techniques may involve a determination of an ideal thin layer formulation. The ideal thin layer formulation includes an optimal amount of a hemostatic drug. The optimal amount of the hemostatic drug is the amount that results in an effective concentration of the hemostatic drug reaching the lining of the uterine cavity 104. In addition to the optimal amount of a hemostatic drug, a number of other factors are considered in determining the ideal thin layer formulation. Some of these other factors may include drug release kinetics, thin layer transfer, transcavitary drug partitioning, drug dissolution rate, and release of unbound active drug.

In a first embodiment of a drug delivery vehicle resulting from a coating technique, the thin layer may contain nanoparticles of the hemostatic drug attached to drug carriers. The carriers may detach from the thin layer and convey the nanoparticles to the lining of the uterine cavity 104. The nanoparticles of the hemostatic drug exert their therapeutic effect and reduce uterine hemorrhaging. The thin layer may include a substance that improves the efficacy of the hemostatic drug. The substance may result in improved absorption of the nanoparticles by the endometrium and a greater bioavailability of the hemostatic drug. The substance may include methacrylic acid copolymer and the like.

In a second embodiment, the drug delivery vehicle may contain one or more layers. Each of the one or more layers may include nanoparticles of a hemostatic drug and one or more excipients. The one or more excipients may control release of the nanoparticles from the one or more layers such that therapeutic levels of the hemostatic drug are maintained at the lining of the uterine cavity 104. The hemostatic drug retards PPH as long as the drug is present at therapeutic levels.

In a third embodiment, liposomes may be contained in the thin layer on the outer surface of an inflated intrauterine balloon 108. Because of their attributes, liposomes are effective drug delivery vehicles. Liposomes are phospholipid vesicles that have one or more concentric lipid bilayers enclosing an aqueous core. This structure allows liposomes to encapsulate lipophilic and hydrophilic drugs. Consequently, liposomes are capable of encapsulating a variety of drugs. Hemostatic drugs may be among the drugs that are encapsulated by liposomes. Furthermore, liposomes can be formulated to function in a variety of drug delivery situations. In particular, the physiochemical and biophysical properties of liposomes can be manipulated to produce liposomes capable of delivering encapsulated drugs to various sites having different prevailing conditions. In the present embodiment, the properties of liposomes may be altered to yield liposomes that deliver encapsulated hemostatic drugs to the hemorrhaging endometrium of the uterine cavity 104.

More specifically, in the present embodiment, liposomes may act as drug delivery vehicles by encapsulating nanoparticles of the hemostatic drug, dissociating from the thin layer on the outer surface of the inflated intrauterine balloon 108, and transporting the encapsulated nanoparticles to the lining of the uterine cavity 104. Upon reaching this site, the nanoparticles are released from the liposomes enabling the nanoparticles to exert their hemostatic effect and stop the uterine hemorrhage.

In a fourth embodiment of a drug delivery vehicle resulting from a coating technique, smart polymers may be contained in the thin layer on the outer surface of the inflated intrauterine balloon 108. Polymers are "smart" if their function as a drug delivery vehicle depends upon sensitivity to stimuli. The present embodiment exploits this sensitivity of smart polymers.

For example, smart polymers may entrap nanoparticles of a hemostatic drug. An alteration in the structure or properties of the smart polymers may occur in response to specific physiological triggers. These changes may result in release of the nanoparticles of the hemostatic drug. The nanoparticles exert their antifibrinolytic effect at the lining of the uterine cavity 104, thereby preventing further hemorrhaging.

Smart polymers can act as a drug delivery vehicle because they exhibit a nonlinear response to a small stimulus. The response is nonlinear in that the small stimulus causes a substantial change in the structure or properties of the smart polymers. These polymers respond to the stimulus in a variety of ways. The responses range from swelling or contracting to disintegration of the smart polymers. In the present embodiment, these responses may result in the release of the entrapped nanoparticles of the hemostatic drug at the juncture of the outer surface of the inflated intrauterine balloon 108 and the lining of the uterine cavity 104.

In a fifth embodiment of a drug delivery vehicle produced by a coating technique, self-propelling particles may be contained in the thin layer on the outer surface of the inflated intrauterine balloon 108. Self-propelling particles may incorporate nanoparticles of a hemostatic drug and convey the incorporated nanoparticles against the flow of blood from a uterine hemorrhage. Because they can move counter to blood flow, self-propelling particles may be effective at treating a severe hemorrhage in the lining of the uterine cavity 104.

The flow of blood from a severe uterine hemorrhage forces the nanoparticles of the hemostatic drug out of the uterus. As a result, the residence time of the hemostatic drug in the uterine cavity 104 is significantly curtailed, the efficacy of the hemostatic drug is reduced, and the severe hemorrhage may continue unabated. Self-propelling particles are capable of autonomous movement and can deliver the nanoparticles of the hemostatic drug to the uterine lining despite the opposing flow of blood from a severe hemorrhage. As a result, the hemostatic drug may be present at the hemorrhage site in therapeutic amounts.

The preceding discussion focuses on various embodiments of the drug delivery vehicle produced by a coating technique. These embodiments may be used individually or in combination. The designation of the embodiments as first, second, etc. is arbitrary.

As discussed above, there are two types of drug delivery vehicles. The two types are drug delivery vehicles resulting from a coating technique and drug delivery vehicles resulting from an eluting technique. There are several differences that should be considered when deciding which type of drug delivery vehicle to use to control PPH. Drug delivery vehicles produced by a coating technique are characterized by the rapid release of nanoparticles of the hemostatic drug and the homogeneous transfer of the nanoparticles to the uterine lining. In contrast, drug delivery vehicles produced by an eluting technique are characterized by the slow release of nanoparticles of the hemostatic drug and the heterogeneous transfer of the nanoparticles to the uterine lining. Furthermore, as discussed above, drug delivery vehicles formed by an eluting technique include a polymer matrix. Fragments may detach from the polymer matrix and become implanted in the uterine lining. The polymer implants may remain after the conclusion of treatment for PPH. By comparison, drug delivery vehicles formed by a coating technique do not result in the implantation of polymer fragments in the uterine lining because drug delivery vehicles of this type lack a polymer matrix.

The device 100 includes a cervical barricade 118. The barricade may be a cone-shaped plug that tapers proximally to conform to the contour of the vagina. The cervical barricade 118 may be located at the cervicovaginal junction 120 to seal the uterine cavity 104. The sealing of the uterine cavity 104 may prevent fast egress of the released hemostatic drug. As a consequence, the hemostatic drug may remain in the uterine cavity 104 long enough to exert its therapeutic effect. The cervical barricade 118 is discussed in detail with respect to FIG. 2.

As shown in FIG. 1, the device 100 may include a catheter 102. The catheter 102 may have an intrauterine section 122, an intravaginal section 124, and an extra-vaginal section 126. The sections may be approximately 120 mm, 110 mm, and 200 mm in length, respectively. The catheter 102 may have an inflation lumen 128 and a drainage lumen 130. The two lumens may be coaxial. A two-way valve 132 may be located in an extracorporeal section of the catheter 102. The two-way valve 132 may have an inflation port (IP) 134 and a drainage port (DP) 136.

The inflation port 134 and the inflation lumen 128 may be connected. To inflate the intrauterine balloon, a sterile liquid may be injected into the inflation port 134 and fill the balloon via the inflation lumen 128. The drainage port 136 and the drainage lumen 130 may be connected. To deflate the intrauterine balloon, the sterile liquid may be withdrawn from the drainage port 136 and exit the balloon via the drainage lumen 130.

The catheter 102 may have a threaded external surface 138 that extends from the mid-vagina to the lower uterine segment 140. An intravaginal portion 142 of the threaded external surface 138 may measure approximately 50 mm in length from mid-vagina to the cervix 144. An intrauterine portion 146 of the threaded external surface 138 may measure approximately 20 mm to 30 mm in length from the cervix 144 to the lower uterine segment 140. However, these dimensions may change to accommodate variations in uterine size.

The catheter 102 may support the cervical barricade 118. In particular, the cervical barricade 118 may move along the threaded external surface 138 of the catheter 102. To accommodate the cervical barricade 118, the threaded external surface 138 may be made of a harder, less flexible first polyurethane polymer. The hardness and the lesser flexibility of the first polyurethane polymer may prevent deformation of the catheter 102 as the cervical barricade 118 moves along the threaded external surface 138. To further enhance durability, the threaded external surface 138 may be more substantial than the external surface of the remainder of the catheter 102. Consequently, the portion of the catheter 102 having the threaded external surface 138 may have an outer diameter 148 of approximately 12 mm while the remainder of the catheter 102 may have an outer diameter that is somewhat smaller.

The remainder of the catheter 102 may be constructed of a second polyurethane polymer that is less hard and more flexible than the first polyurethane polymer. The lesser hardness and the greater flexibility of the second polyurethane polymer may enable manipulation of the catheter 102 during insertion and removal.

Figure 2:
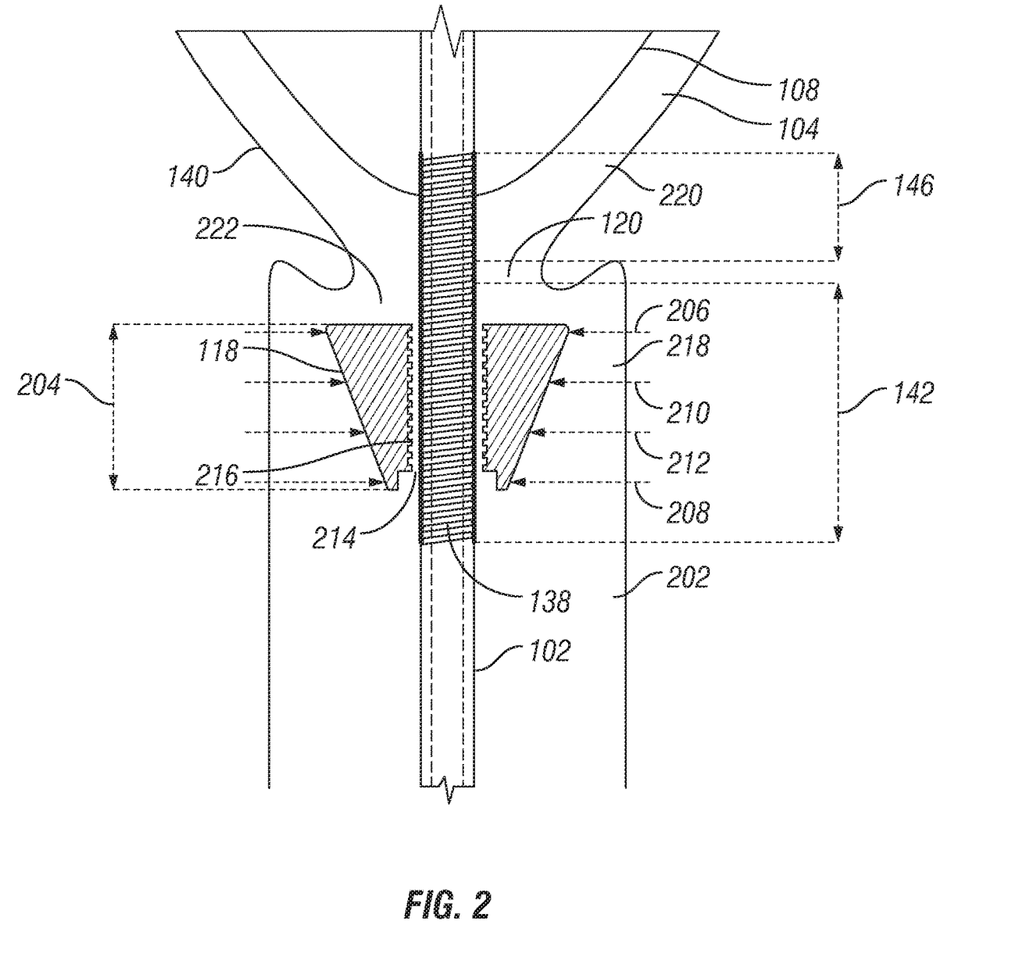
FIG. 2 is an illustration of a cervical barricade that is a component of the device for the management of postpartum hemorrhage.

FIG. 2 is an illustration of the cervical barricade that is a component of the device for the management of postpartum hemorrhage. The cervical barricade 118 may be a cone-shaped plug. Alternatively, the cervical barricade 118 may have any other shape that conforms to the contours of the vagina 202. Because of its design, the cervical barricade 118 is easily manipulated intravaginally.

The cervical barricade 118 may weigh approximately 200 gm to 300 gm and may measure approximately 40 mm in length 204. Additionally, the cervical barricade 118 may taper proximally. Accordingly, the cervical barricade 118 may narrow from a diameter of approximately 30 mm at its distal end 206 to a diameter of approximately 15 mm at its proximal end 208. Intermediate diameters 210, 212 may measure approximately 25 mm and 20 mm.

A cylindrical opening 214 may extend longitudinally through the center of the cervical barricade 118. The cylindrical opening 214 may accommodate the catheter 102, i.e., the catheter 102 may fit through the cylindrical opening 214. A threaded inner surface 216 of the cervical barricade 118 may enable the cervical barricade 118 to be moved along the threaded external surface 138 of the catheter 102. The cervical barricade 118 may move distally along the intravaginal portion 142 of the threaded external surface 138 until the cervical barricade 118 is located at the cervicovaginal junction 120 and seals the uterine cavity 104. However, the cervical barricade 118 may have to move beyond the cervicovaginal junction 120 and continue along the intrauterine portion 146 of the threaded external surface 138 before the uterine cavity 104 is sealed. In this manner, the cervical barricade 118 may accommodate variations in the length of the uterine cavity 104.

The cervical barricade 118 may be constructed of the same first polyurethane polymer as the threaded external surface 138 of the catheter 102. The properties of the first polyurethane polymer that make it an appropriate material of construction for the threaded external surface 138 may make it an appropriate material of construction for the cervical barricade 118. The first polyurethane polymer may be inert and non-toxic which may render the cervical barricade 118 suitable for intracorporeal use. Furthermore, the hardness and the lesser flexibility of the first polyurethane polymer may prevent deformation of the cervical barricade 118 as it moves along the threaded external surface 138 of the catheter 102 and contacts the contours of the distal end 218 of the vagina 202 and the proximal end 220 of the uterine cavity 104.

The cervical barricade 118 may be located at the cervicovaginal junction 120 to seal the uterine cavity 104. The sealing of the uterine cavity 104 may prevent fast egress of the released hemostatic drug. As a consequence, the hemostatic drug may remain in the uterine cavity 104 long enough to exert its therapeutic effect.

The uterine cavity 104 may be completely sealed by the cervical barricade 118. Consequently, the effectiveness of the device 100 in stopping PPH cannot be determined by visually examining the vagina 202 for the presence of blood. The extent of the hemorrhage beyond the cervical barricade 118 cannot be established without the aid of ultrasound imaging. Hence, ultrasound imaging is necessary to monitor the course of a uterine hemorrhage. However, the cervical barricade 118 may have two small openings that can be used to determine the extent of a uterine hemorrhage. The two small openings may be located opposite one another in the periphery of the distal end 206 of the cervical barricade 118. The amount of blood seeping through the openings may indicate the severity of an ongoing hemorrhage. As the device 100 exerts its therapeutic effects, the seepage may decrease and cease altogether.

The cervical barricade 118 may immobilize the inflated intrauterine balloon 108 in the uterine cavity 104. The immobilized intrauterine balloon may serve two purposes. First, the outer surface of the inflated intrauterine balloon 108 may remain in contact with the lining of the uterine cavity 104. Because of this apposition, the outer surface of the inflated intrauterine balloon 108 may apply pressure to the lining of the uterine cavity 104. Second, the released hemostatic drug may have less distance to travel to reach the uterine lining and exert its therapeutic effect. The combination of the mechanical and pharmacological functions of the cervical barricade 118 may control PPH.

There may be another reason for using the cervical barricade 118 to immobilize the inflated intrauterine balloon 108 in the uterine cavity 104. The immobilizing action of the cervical barricade 118 may eliminate the need to secure the inflated intrauterine balloon 108 by other means. For example, it may no longer be necessary to fasten the extracorporeal section of the catheter 102 to the patient's leg. Additionally, the need to attach a weight to the external portion of the catheter 102 may be avoided.

The cervical barricade 118 may apply additional counter pressure (pressure supplementing that exerted by the inflated intrauterine balloon 108) to the lower uterine segment (LUS) 140. As a result, hemorrhaging from the LUS 140 may be arrested. There are two conditions that can cause the LUS 140 to hemorrhage. The first condition is placenta previa which occurs when the placenta partially or totally covers the cervical opening 222. Hemorrhaging often occurs at the LUS 140 because the LUS 140 thins during the third trimester in preparation for the onset of labor. The severity of the hemorrhage from the LUS 140 depends upon the extent to which the cervical opening 222 is covered by the placenta. Hemorrhaging becomes more severe as the placenta covers a greater area of the cervical opening 222.

Placenta accreta is the other condition that can cause hemorrhage of the LUS 140. This condition occurs when the placenta grows too deeply into the uterine wall and fails to detach after birth. The abnormally adherent placenta can cause severe blood loss after delivery. The LUS 140 can be the site of the bleeding. As discussed above, the device 100 may apply pressure to the LUS 140 in two ways. First, the inflated intrauterine balloon 108 may contact the LUS 140 and exert pressure on the LUS 140 because of the immobilizing and stabilizing characteristics of the cervical barricade 118. Second, when located at the cervicovaginal junction 120, the cervical barricade 118 may also apply pressure to the LUS 140. The effects of the inflated intrauterine balloon 108 and the cervical barricade 118 may combine to stop the LUS 140 from hemorrhaging.

An embodiment is an implementation or example. Reference in the specification to "an embodiment," "one embodiment," "some embodiments," "various embodiments," or "other embodiments" means that a particular feature, structure, or characteristic is included in at least some embodiments, but not necessarily all embodiments, of the present device. The various discussions of "an embodiment," "one embodiment," or "some embodiments" are not necessarily referring to the same embodiments.

Not all components, features, structures, characteristics, etc. described and illustrated herein need be included in a particular embodiment or embodiments. If the specification states a component, feature, structure, or characteristic "may," "might," "can," or "could" be included, for example, that particular component, feature, structure, or characteristic is not required to be included. If the specification or a claim refers to "a" or "an" element, that does not mean there is only one of the element. If the specification or a claim refers to "an additional" element, that does not preclude the possibility that there may be more than one of the additional element.

Although some embodiments have been described in reference to particular implementations, other implementations are possible according to the same embodiments. Additionally, features illustrated in the drawings or described herein need not be arranged in the particular way illustrated or described. Other arrangements are possible.

In each system shown in a figure, the elements may have the same reference numbers or different reference numbers to suggest that the elements represented could be similar or different. However, an element may be flexible enough to have different implementations and may work with some or all of the systems shown or described herein. The various elements shown in the figures may be the same or different. It is arbitrary which element is referred to as a first element and which is called a second element.

The present device is not restricted to the particular details listed herein. Indeed, those skilled in the art having the benefit of this disclosure will appreciate that many other variations from the foregoing descriptions and drawings may be made that are within the scope of the present device. Accordingly, it is the following claims, including any amendments thereto, that define the scope of the present device.

The invention claimed is:

1. A device for managing postpartum hemorrhage, comprising:
    an intrauterine balloon to insert into a uterine cavity, wherein the intrauterine balloon is deflated when inserted into the uterine cavity and is inflated inside the uterine cavity to obtain an inflated intrauterine balloon;
    a drug delivery vehicle deposited on an outer surface of the intrauterine balloon by a coating technique or an eluting technique, wherein the drug delivery vehicle releases a hemostatic drug into the uterine cavity to obtain a released hemostatic drug;
    a catheter to inflate and deflate the intrauterine balloon, wherein a threaded external surface of the catheter extends from mid-vagina to a lower uterine segment; and
    a cervical barricade comprising a cylindrical opening to accommodate the catheter, wherein the cervical barricade has a threaded inner surface to allow the cervical barricade to move along the threaded external surface of the catheter and wherein the cervical barricade comprises a cone-shaped plug that seals the uterine cavity when the cervical barricade is located at a cervicovaginal junction such that the released hemostatic drug is retained in the uterine cavity.

2. The device of claim 1, wherein the catheter comprises an inflation lumen and a drainage lumen and the inflation lumen and the drainage lumen are coaxial and wherein a two-way valve is located in an extracorporeal section of the catheter, the two-way valve has an inflation port associated with the inflation lumen for inflating the intrauterine balloon and a drainage port associated with the drainage lumen for deflating the intrauterine balloon.

3. The device of claim 1, wherein the inflated intrauterine balloon tapers proximally to conform to the uterine cavity such that the outer surface of the inflated intrauterine balloon contacts a uterine lining to apply pressure to the uterine lining to aid in arresting hemorrhage from the uterine lining.

4. The device of claim 1, wherein the threaded external surface of the catheter comprises a first polyurethane polymer, a remainder of the catheter comprises a second polyurethane polymer, and the first polyurethane polymer is harder than the second polyurethane polymer.

5. The device of claim 4, wherein the cervical barricade comprises the first polyurethane polymer and wherein the cylindrical opening extends longitudinally through the center of the cervical barricade.

6. The device of claim 1, wherein the cervical barricade is located at the cervicovaginal junction to immobilize the inflated intrauterine balloon in the uterine cavity such that the outer surface of the inflated intrauterine balloon remains in contact with the uterine lining and wherein the cervical barricade is located at the cervicovaginal junction to apply pressure to the lower uterine segment to aid in arresting hemorrhage from the lower uterine segment caused by placenta previa or placenta accreta.

7. The device of claim 1, wherein the drug delivery vehicle comprises a polymer matrix, nanoparticles of the hemostatic drug associated with the polymer matrix, a first constituent, and a second constituent, wherein the first constituent and the second constituent interact to release the nanoparticles of the hemostatic drug from the polymer matrix into the uterine cavity.

8. The device of claim 7, wherein the polymer matrix comprises hydroxypropyl cellulose phthalate, hydroxypropyl methylcellulose phthalate, cellulose acetate phthalate, polyvinyl acetate phthalate, or polyvinylpyrrolidone acetate.

9. The device of claim 1, wherein the drug delivery vehicle comprises the nanoparticles of the hemostatic drug attached to a carrier and the carrier conveys the nanoparticles of the hemostatic drug to the uterine lining.

10. The device of claim 9, further comprising a substance to facilitate absorption of the nanoparticles of the hemostatic drug by the uterine lining.

11. The device of claim 10, wherein the substance comprises methacrylic acid copolymer.

12. The device of claim 1, wherein the drug delivery vehicle comprises one or more layers of the hemostatic drug and one or more excipients and the one or more excipients control release of the hemostatic drug into the uterine cavity.

13. The device of claim 1, wherein the drug delivery vehicle comprises a liposome, the nanoparticles of the hemostatic drug are encapsulated by the liposome, and the liposome transports the nanoparticles of the hemostatic drug to the uterine lining where the nanoparticles of the hemostatic drug are released from the liposome.

14. The device of claim 1, wherein the drug delivery vehicle comprises a smart polymer, the nanoparticles of the hemostatic drug are entrapped by the smart polymer, an alteration in a structure or a property of the smart polymer occurs in response to a physiological trigger, and the alteration in the structure or the property of the smart polymer results in release of the nanoparticles of the hemostatic drug into the uterine cavity.

15. The device of claim 1, wherein the drug delivery vehicle comprises a self-propelling particle, the nanoparticles of the hemostatic drug are incorporated into the self-propelling particle, and the self-propelling particle moves counter to a flow of blood from a uterine hemorrhage to deliver the nanoparticles of the hemostatic drug to the uterine lining.

16. The device of claim 1, wherein the hemostatic drug comprises tranexamic acid, thrombin, fibrinogen, or recombinant activated factor VII.

* * * * *